United States Patent
McCartney

(12) 
(10) Patent No.: US 6,572,631 B1
(45) Date of Patent: Jun. 3, 2003

(54) TRANSVAGINAL TUBE AS AN AID TO LAPAROSCOPIC SURGERY

(75) Inventor: Anthony John McCartney, Swanbourne (AU)

(73) Assignee: Gynetech Pty Ltd. (AU)

( * ) Notice: Subject to any disclaimer, the term of this patent is extended or adjusted under 35 U.S.C. 154(b) by 0 days.

(21) Appl. No.: 09/443,503

(22) Filed: Nov. 19, 1999

Related U.S. Application Data

(63) Continuation-in-part of application No. 08/586,856, filed as application No. PCT/AU94/00630 on Oct. 13, 1994.

(30) Foreign Application Priority Data

Oct. 22, 1993 (GB) .............................................. 9321773
May 31, 1994 (AU) ............................................. PM 6015

(51) Int. Cl.$^7$ .......................... A61B 17/42; A61B 17/32
(52) U.S. Cl. ....................................... 606/167; 606/119
(58) Field of Search ................................ 606/167, 185, 606/128, 119; 604/158, 264, 27, 30, 34, 35; 600/138, 153–154, 105, 104

(56) References Cited

U.S. PATENT DOCUMENTS

| | | | |
|---|---|---|---|
| 3,075,516 A | * | 1/1963 | Strauch |
| 3,542,031 A | | 11/1970 | Taylor |
| 3,890,976 A | * | 6/1975 | Bazell et al. |
| 4,000,743 A | | 1/1977 | Weaver |
| 4,046,140 A | * | 9/1977 | Born |
| 4,112,932 A | | 9/1978 | Chiulli |
| 4,715,360 A | * | 12/1987 | Akui et al. |
| 4,997,419 A | | 3/1991 | Lakatos et al. |
| 5,108,408 A | | 4/1992 | Lally |
| 5,141,498 A | * | 8/1992 | Christian |
| 5,147,315 A | * | 9/1992 | Weber |
| 5,209,754 A | | 5/1993 | Ahluwalia |
| 5,256,149 A | * | 10/1993 | Banik et al. |
| 5,364,365 A | * | 11/1994 | Wortrich |
| 5,368,598 A | | 11/1994 | Hasson |
| 5,382,252 A | | 1/1995 | Failla et al. |
| 5,383,861 A | | 1/1995 | Hempel et al. |
| 5,387,197 A | * | 2/1995 | Smith et al. |

(List continued on next page.)

FOREIGN PATENT DOCUMENTS

| | | |
|---|---|---|
| AU | 3786 | 9/1921 |
| EP | 0400458 | 12/1990 |
| EP | 0407057 | 1/1991 |
| EP | 0615727 | 9/1994 |
| FR | 2697989 | 5/1994 |
| WO | 8606968 | 12/1986 |
| WO | 9324063 | 12/1993 |
| WO | 9400061 | 1/1994 |
| WO | 9410926 | 5/1994 |

OTHER PUBLICATIONS

Koh, C.H., *The Colpotomy Optimized Hysterectomy*, "A New System for Total Laparoscopic Hysterectomy Using the Rowden Uterine Manipulator Injector (RUMI) with the Koh Colpotomizer and Pneumo–occluder" 7 pages.

*Primary Examiner*—Michael J. Milano
*Assistant Examiner*—Jessica R Baxter
(74) *Attorney, Agent, or Firm*—Rothwell, Figg, Ernst & Manbeck

(57) ABSTRACT

A transvaginal tube adapted for insertion into the vaginal tract of a patient for use during performance of a laparoscopic hysterectomy or other laparoscopic surgery on the patient. The tube has a diameter greater than the patient's cervix opening and has a distal end and a proximal end. The proximal end is cut in a plane non-normal to its tubular axis being adapted to define the patient's cervico-vaginal junction. The tube further includes a sealing structure capable of forming a seal at the distal end of the tube during the surgery. The tube is capable of maintaining the pneumoperitoneum when inserted into the vaginal tract of the patient with the seal formed at the distal end of the tube.

56 Claims, 6 Drawing Sheets

U.S. PATENT DOCUMENTS

| | | | |
|---|---|---|---|
| 5,392,765 A | * | 2/1995 | Muller |
| 5,401,248 A | | 3/1995 | Bencini |
| 5,407,427 A | * | 4/1995 | Zhu et al. |
| 5,445,168 A | | 8/1995 | Krebs |
| 5,460,615 A | | 10/1995 | Storz |
| 5,464,409 A | | 11/1995 | Mohajer |
| 5,562,680 A | | 10/1996 | Hasson |
| 5,746,750 A | | 5/1998 | Prestel et al. |

* cited by examiner

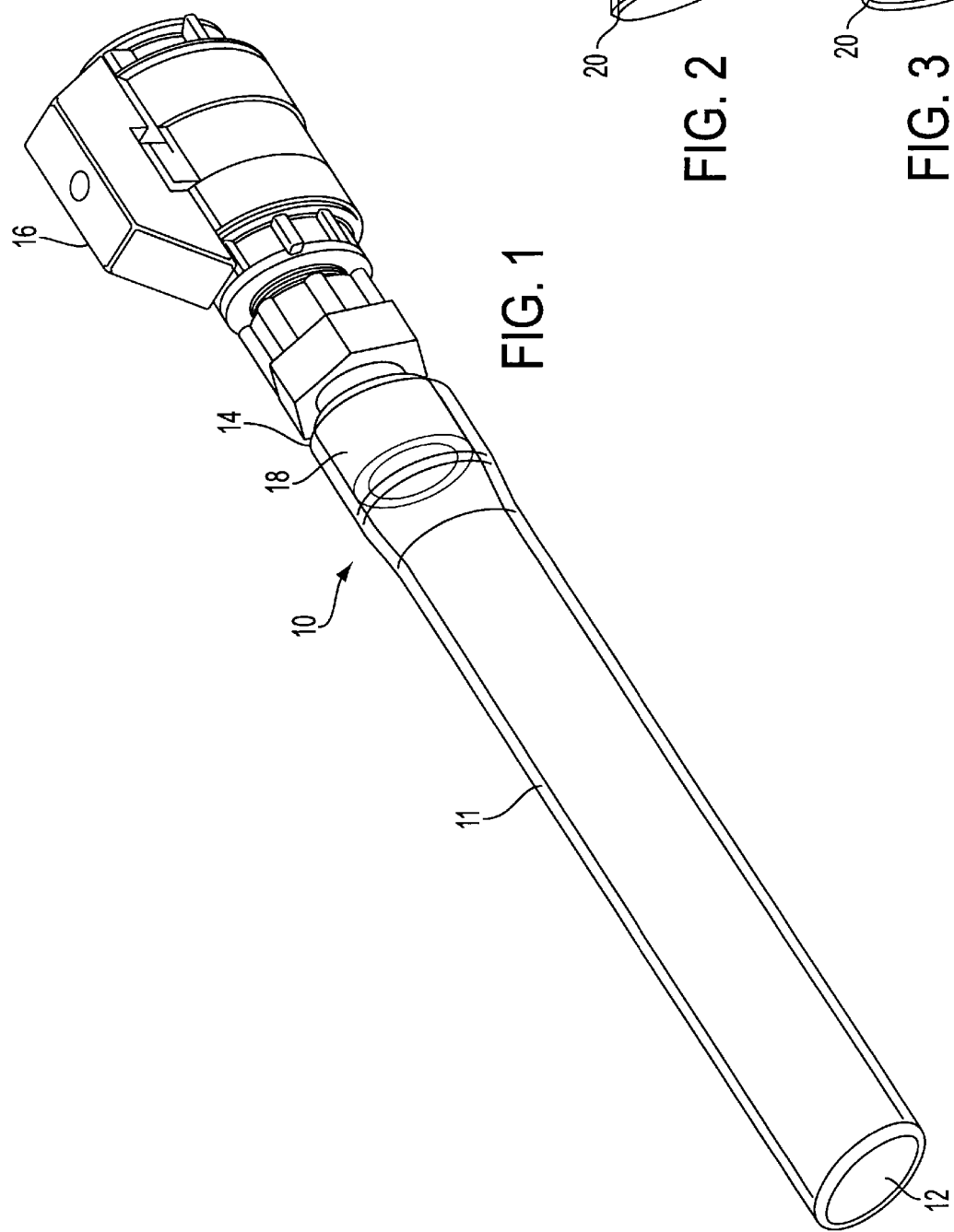

TRANSVAGINAL TUBE AS AN AID TO LAPAROSCOPIC SURGERY

CROSS-REFERENCE TO RELATED TO APPLICATIONS

This application is a continuation-in-part of U.S. Ser. No. 08/586,856 having a 35 U.S.C. §102(e) filing date of Feb. 4, 1998, now abandoned which is a 35 U.S.C. §371 application of PCT/AU94/00630, filed Oct. 13, 1994.

FIELD OF THE INVENTION

This invention relates to transvaginal tube which is particularly useful in laparoscopic surgery, and also to a procedure for the use of such a tube.

BACKGROUND ART

Modern advances in laparoscopic surgical equipment have meant that surgeons are able to remove the uterus and/or ovaries laparoscopically, removing the need for a long abdominal incision.

A laparoscopic radical hysterectomy for cancer has evolved from the efforts of a few oncology centres with an interest in minimising invasive surgery. The operative technique is analogous to a modification of the operation originally described by Wertheim and Meigs. The laparoscope surgeon passes a 10 mm laparoscope trans-abdominally through a sub-umbilical incision after establishing a pneumoperitineum. Using two lateral portals the ovarian pedicles are divided down to the level of the uterine arteries. The ureter is isolated and protected and the uterine vessels and parametrium are divided after mobilising the bladder. The next stage is to remove the uterus and close the vaginal vault so the pneumoperitoneum can be re-established for the lymphadenectomy. The lymph nodes are removed by plucking them from their bed and dragging them out of the abdomen through the trans-abdominal wall port used for the grasping forceps.

Various medical commentators suggest that laparoscopically assisted radical hysterectomy (colloquially known as "keyhole Wertheims") offers many advantages. Patients go home earlier and the convalescence period is shorter. The disadvantage is that the additional laparoscopic surgery increases operative time.

Plastic bags have been used to harvest ovaries in an attempt to minimise the contamination of metastatic material through the ports. However, these are fiddly to use and can be difficult to drag out of the abdominal port. Nonetheless, one study has demonstrated that ordinary plastic bags are just as effective as commercially available customised bags and ovaries and omentum can be placed in a bag and delivered through the vagina. This is an excellent refinement for ovarian surgery but it is difficult to place multiple small nodes in several bags and be sure of their origin.

SUMMARY OF THE INVENTION

The present invention provides a transvaginal tube, and a procedure for using that tube, which is suitable for use in laparoscopic surgical techniques.

According to one aspect, the present invention provides a transvaginal tube adapted for insertion into the vaginal tract for the exteriorization of intra-abdominal tissue, the tube having a diameter greater than the cervix opening and having a distal end and a proximal end, the proximal end being cut in a plane non-normal to the tubular axis and being adapted to define a cervico-vagnial junction.

Preferably, the proximal end of the transvaginal tube is bevelled so that the leading or anterior edge of the tube protrudes beyond the posterior edge. In this respect, the anterior edge is, for example, 1 to 2 cm longer than the posterior edge. To avoid tissue damage in use, the edge of the tube surrounding the open bevelled end may be adapted to have a smooth edge. This may, for example, be achieved by moulding or shaping the tube with smooth convex edges or by attaching a cover means to the proximal end of the tube walls which blankets and provides a smooth surface over the wall of the bevelled open end of the tube.

The transvaginal tube may be formed of any material. However, the tube is preferably made of a plastic material which provides a degree of flexibility.

Preferably, the tube is also substantially transparent. It will be appreciated that the tube may be formed of opaque material but may contain one or more transparent portals along the length of the tube.

The tube may be of any length and diameter. Preferably the tube is of a greater length than 5 cm and has a diameter of from 10 to 100 mm. More preferably, the tube is 25 to 50 cm in length and has a diameter of from 30 to 50 mm.

To facilitate use in a sterile environment, the transvaginal tube is preferably capable of withstanding sterilization and the distal end of the tube may be sealed or open. Any means known in the art which is capable of sealing the distal end of the tube may be employed in the invention. For example, the distal end may be capped or plugged. Preferably the sealing means is capable of effecting a fluid tight closure of the distal end of the tube to approximately 5 to 30 cm of water pressure but most preferably 15 cm of water pressure.

Alternatively, the distal end of the tube may be in a releasable sealing engagement with a at least a valve means which when closed is capable of forming a fluid tight enclosure at the distal end of the tube to approximately 5 to 30 cm of water pressure, and most preferably to 15 cm of water pressure. Any valve means known in the art which is capable of achieving this may be employed in the invention. To facilitate use in a sterile environment, the valve means is preferably capable of withstanding sterilization.

When the distal end of the transvaginal tube is open, one or more smaller bore tubes may be inserted into the transvaginal tube. For example, a smaller bore tube may be fitted into the end of the transvaginal tube to promote washing of body fluids and tissue specimens from the proximal end of the interior of the transvaginal tube into a plastic collection bowl with or without the aid of suction when the transvaginal tube is fitted within a subject. Alternatively there may be passed into the transvaginal tube an intra-uterine manipulator which is longer than the internal length of the tube and which may be fixed by aids to the inside of the tube. The distal end of this manipulator may be used to enter the cervix to allow manipulation of the cervix throughout the surgical procedure of hysterectomy or adnexal surgery.

In another embodiment of the invention there is fixed in a concentric arrangement within the transvaginal tube a fluid tight channel through which a telescope or light sources may be inserted while maintaining fluid pressure within the tube. Preferably that channel extends from the distal end to the proximal end of the tube. The channel may be sealed at the distal end of the tube. Alternatively, the distal end of the tube may be adapted to house a portal which is capable of forming a releasable sealing engagement with the circumferential rim of the distal open end of the channel providing the interior of the channel with a means of communication with the exterior of the tube. The proximal end of the channel is preferably sealed.

Desirably the releasable sealing engagement between the tube and the channel should be capable of withstanding approximately 5 to 30 cm of water pressure but most preferably 15 cm of water pressure. While such a channel may be suitable for telescopes and light sources it will be appreciated that other surgical instruments may be inserted in the channel.

In a further embodiment, when the interior of the channel is in communication with the exterior of the tube there is preferably provided at least a valve means inserted in the longitudinal wall of the tube. The valve means should be capable of withstanding 5 to 30 cm of water pressure but most preferably 15 cm of water pressure.

In yet a further embodiment of the invention there is releasably engaged to the longitudinal wall of the tube at least a valve means and there is passed to concentric arrangement through the distal end or longitudinal wall of the transvaginal tube and extending the length of the tube, smaller bore tubes which may, for example, provide passage for intra-uterine manipulators, tubes to promote irrigation of tissue, laparoscopic grasping forceps, laparoscopically directed stapling devices or laparoscopically directed electro-coagulation diathermy, laser or ultrasonic scalpel devices. To facilitate use in a sterile environment the tube is preferably sealed at the distal end and is preferably capable of withstanding sterilization. Any means known in the art for sealing the valve means and the smaller bore tubes may be employed with the invention. Preferably the tube comprises at least a valve means and one or more narrow diameter tubes, and when sealed at its distal end, is capable of withstanding approximately 5 to 30 cm of water pressure but most preferably 15 cm of water pressure.

The pressure invention may be employed in laparoscopic surgery for exposure of the vaginal fornices, as an aid to separation of the bladder from the vagina, for division of the vagina by electro-coagulation diathermy, laser or ultrasonic scalpel, and as a conduit for exteriorising tissue from the abdominal pelvic cavity. In this respect, the tissue may be the uterus and/or its adnexal, ovarian cysts, and particular pelvic lymph nodes. The present invention may also be employed as an exit for fluid such as blood and irrigation fluid and smoke or vapour from the abdominal pelvic cavity, as a splinting device to present and expose the dividing edges of the vagina, to facilitate suture closure as a splinting device in the vagina, to expose the vaginal fornices and lateral edge at bladder neck surgery, for insertion of sling devices and as a portal for telescopes or light tubes into the vagina while keeping them separate from the vaginal wall and exposing the vaginal mucoso through the substantially transparent walls of or transparent portals in the tube.

The tube may be used to outline the vagina at open surgery. In these cases the valved end (distal) is not required.

According to a second aspect of the invention there is provided a method for laparoscopic hysterectomy treatment comprising the steps of:
 (i) introducing a tube as aforedescribed into the vagina of a patient so that the proximal end of the tube circumscribes the cervico-vaginal junction;
 (ii) separating the cervix from the vagina; and
 (iii) mobilizing a surgical specimen and inserting it into the proximal end of the tube.

Preferably the cervix is separated from the vagina by the steps of:
 (i) exposing and holding the cervix with laparoscopic grasping manipulators;
 (ii) inserting a knife or diathermy knife to the proximal end of the tube;
 (iii) rotating the tube so the plane non-normal to the tubular axis stretches the vagina and at the same time cutting the cervico-vaginal junction as the tube is rotated.

As well as being most commonly used for simple laparoscopic hysterectomy, the present invention may also be used in laparoscopic radical hysterectomy and pelvic lymph node dissection.

BRIEF DESCRIPTION OF THE DRAWINGS

The present invention will now be described in relation to various examples, which in turn refer to the embodiments of the transvaginal tube as illustrated in the FIGS. 1 to 3. However, it must be appreciated that the following description is not to limit the generality of the above description.

The invention will be more fully understood in the light of the following description of two specific embodiments. The description is made with reference to the accompanying drawings in which:

FIG. 1 is an isometric view of a transvaginal tube according to a first embodiment of the invention;

FIGS. 2 and 3 are sectional views of the proximal end of the transvaginal tube shown in FIG. 1;

Figure 4:
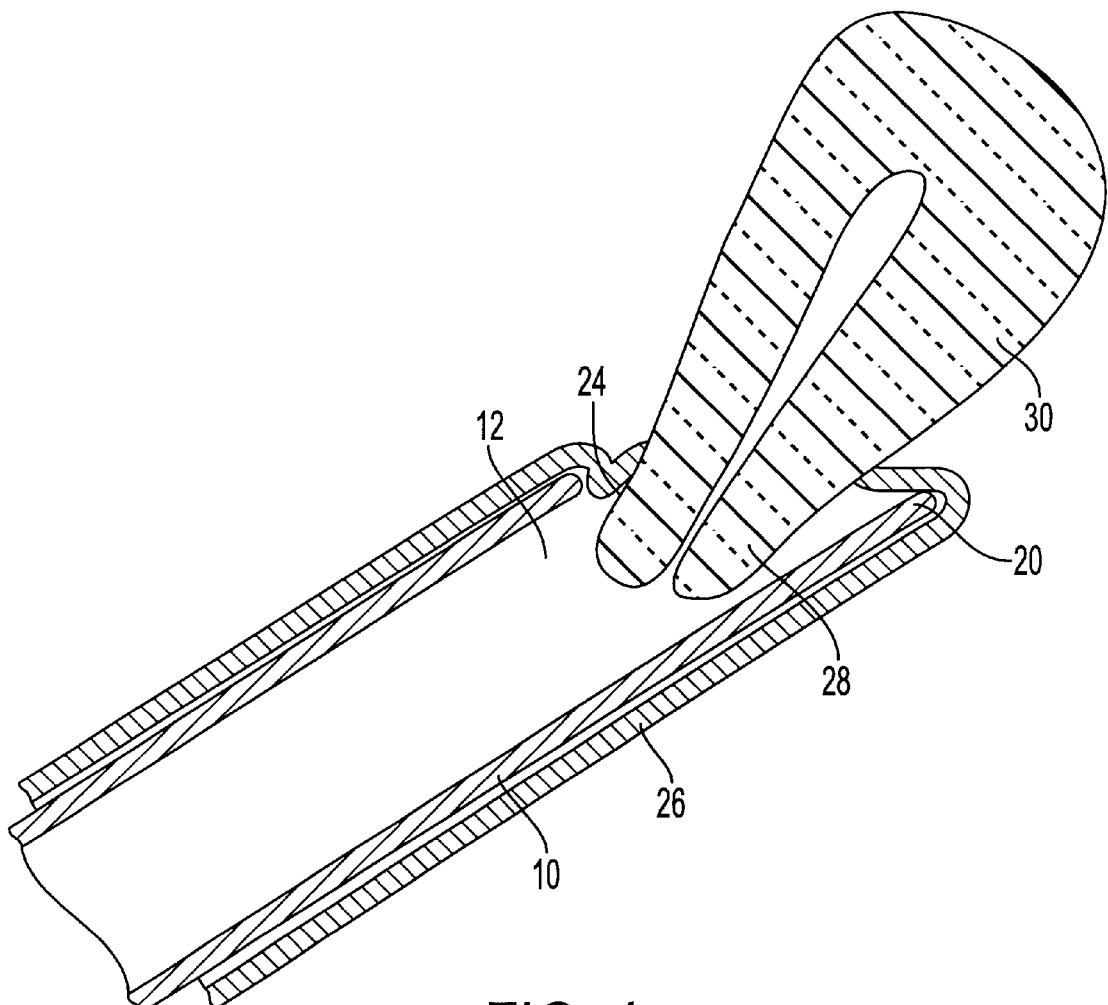
FIG. 4 is a sectional view of the proximal end of the transvaginal tube of FIG. 1 in situ.
Figure 5:
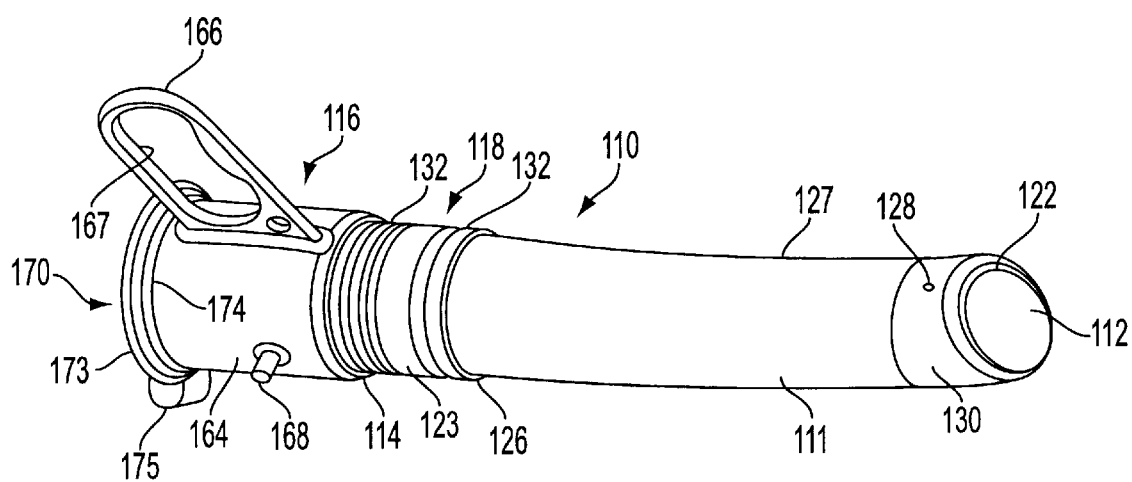
FIG. 5 is a view similar to FIG. 1 of a transvaginal tube according to a second embodiment of the invention.
Figure 8:
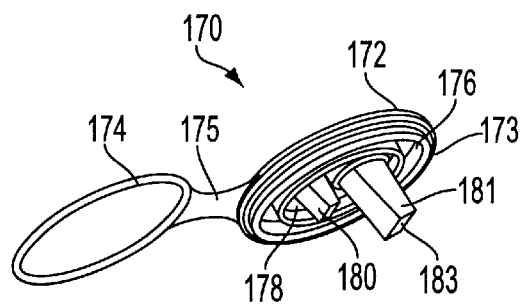
FIG. 8 is an isometric view of the headcap of the embodiment of FIGS. 5 to 7.

The embodiment of FIGS. 1 to 3 relates to a transvaginal tube 10 which has a body defined by a tube 11 which has a proximal end 12 and a distal end 14. The distal end 14 engages a valve means or headpiece 16 at a junction 18. The tube body 11 is a relatively stiff yet flexible plastic material such as polypropylene. Alternatively, a medical grade liquid silicone rubber is suitable. The junction 18 is provided by the resilience of the plastic material allowing for a force fit engagement of the distal end 14 of the tube 10 with one end of the valve means 16 so as to provide a substantially fluid tight engagement.

FIGS. 2 and 3 show sectional side views of the proximal end 12 of the tube 10 including an anterior edge 20 and a posterior edge 22. It will thus be apparent that the proximal end 12 is cut at an angle non-normal to the longitudinal axis of the tube. This provides the bevelled appearance that is apparent in FIGS. 2 and 3 and results in the anterior edge 20 being 1.5 cm beyond the posterior edge 22.

FIG. 4 shows the proximal end 12 of the tube 10 located insitu at the cervico-vaginal junction 24. When located in this position, the vaginal walls 26 envelop the tube 10 forming a seal around the tube. The cervix 28 protrudes into the proximal end 12 of the tube 10 and the uterus 30 lies above and exterior to the anterior edge 20. Thus it will be apparent that the proximal end 12 is adapted to circumscribe the cervico-vaginal junction.

A second embodiment of transvaginal tube 110 is illustrated in FIGS. 5 to 8 and again includes a tube body 111, of material similar to tube body 11, having a proximal end 112 and a distal end 114. Distal end 114 engages a valve means or headpiece 116 in a force fit at a junction 118. Proximal end 112 is again cut at an angle inclined to the normal to the longitudinal axis 125 of the tube, insitu, this end 112 circumscribes the cervico-vaginal junction in the manner depicted in FIG. 4 for the first embodiment.

This section embodiment differs from the first in several respects. Most apparent is the very slight (large radius) curvature of the tube body 111 and of its longitudinal axis 125, except for an end region 123 at distal end 114 that serves as a socket for headpiece 116, so that posterior edge 122 at proximal end 112 is on the inside of the curve. The longitudinal axis 125 of the tube body 111 has a radius of curvature that generally follows the curve of the pelvic axis. This large radius curvature enhances both the ease of insertion of the tube and the reliability of engagement of proximal end 112 about the cervico-vaginal junction, and has the advantage that it presents the proximal end 112 up to the examining surgeon working in the abdominal cavity.

Figure 6:
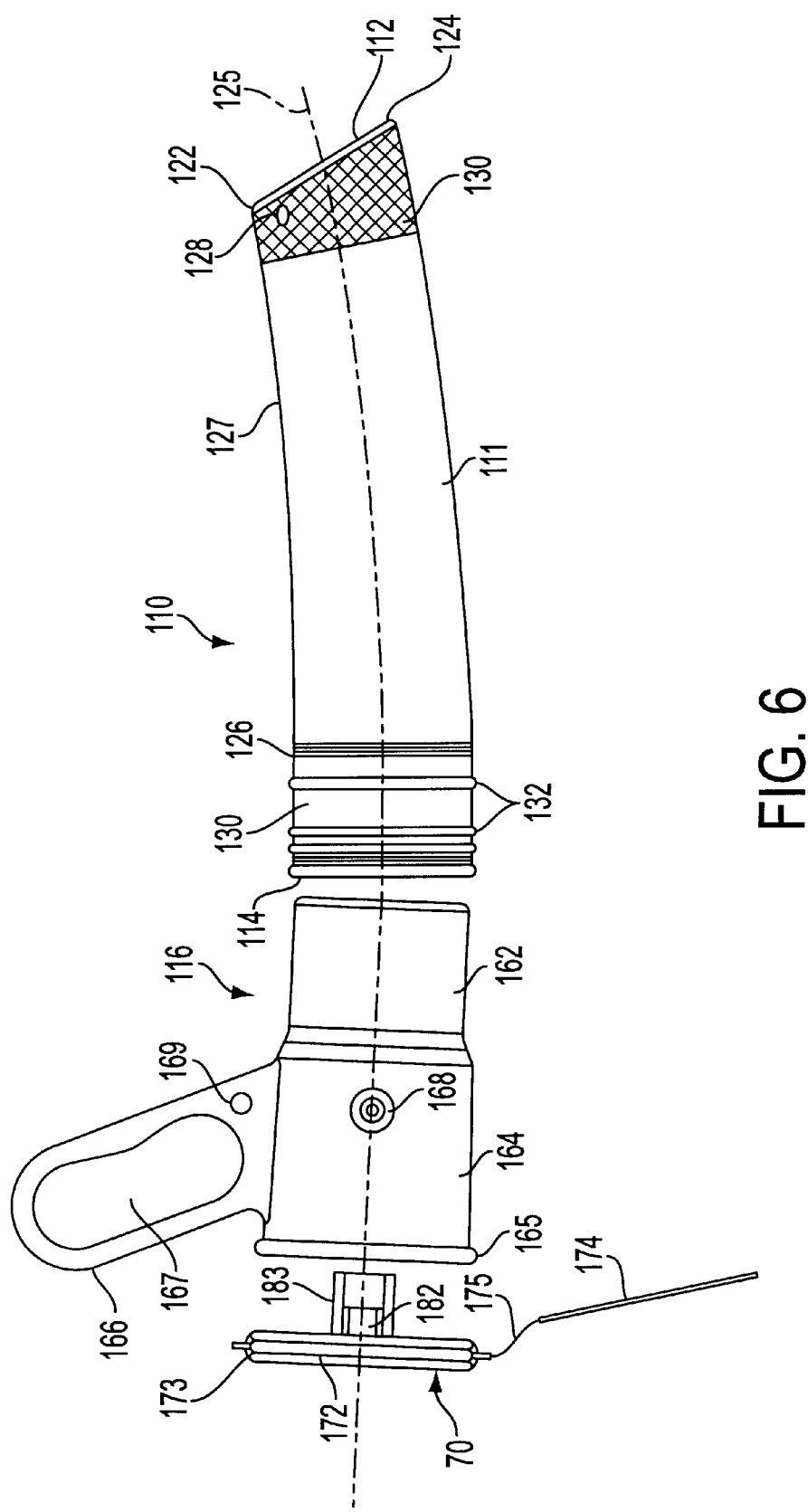
FIG. 6 is a fragmentary side elevational view of the tube depicted in FIG. 5, showing the tube body, the headpiece, and the headcap as separated components.

It is preferred that most tube body 111 is transparent and externally smooth, save for an externally slightly roughened and therefore frosted or opaque region 130 adjacent proximal end 112, indicated by cross-hatching in FIG. 6. This region 130 grips the vagina better and thereby aids in presenting the vagina for suture closure.

Socket end region 123 is straight and made relatively rigid compared to tube body 111 by several integral annular external ribs 132, to enhance the press-fit about a smaller diameter spigot end 162 of headpiece 116. The rest of tube body 111 is substantially stiff but exhibits a degree of flexibility and deformability to facilitate vaginal insertion, and to prevent damage to the vaginal walls that a rigid tube might cause. Tube body 111 is slightly tapered, ie of progressively diminishing thickness—from a stepped peripheral shoulder 126 marking the inner edge of socket end region 123 to a point 127 a little more than half-way along the tube body. This taper initially facilitates mould extraction, but is also thought to be useful for imparting a grated pressure on the vaginal walls to prevent gas loss. Tube body 111 also carries a small circular aperture 128 close to proximal end 112 that is provided as an end-point for a suture holding slit should a surgeon wish to cut such a slit for a given procedure: the aperture will guard against running of the slit as a tear along the tube.

Headpiece 116 may be moulded in, eg, medical grade polyproplene and has a generally tubular, larger diameter main body 164 linked to the aforementioned spigot end 162 of smaller diameter. Both are of annular cross-section. Main body 164 has an externally flat web handle 166, with cutout 167, on a diametral plane, and an external radial nipple 168 to receive a cap or a 2-way bleeder valve for smoke or gas evacuation to an underwater seal. Nipple 168 is normally internally closed. Handle 166 facilitates insertion and positioning of tube 110 during surgery, and is furthermore positioned in a manner enabling it to serve as an orientation node for the tube when introduced into a patient: it is aligned with slot 129 and posterior edge 122. A small hole 169 in handle 166 is useful for attachment of retention tapes to prevent the tube falling out of the vagina.

The rear or outer open end of main body 164 of headpiece 116 is selectively sealingly closed by a headcap 170 comprising a moulding of a highly flexible material such as medical grade liquid silicone rubber.

Figure 7:
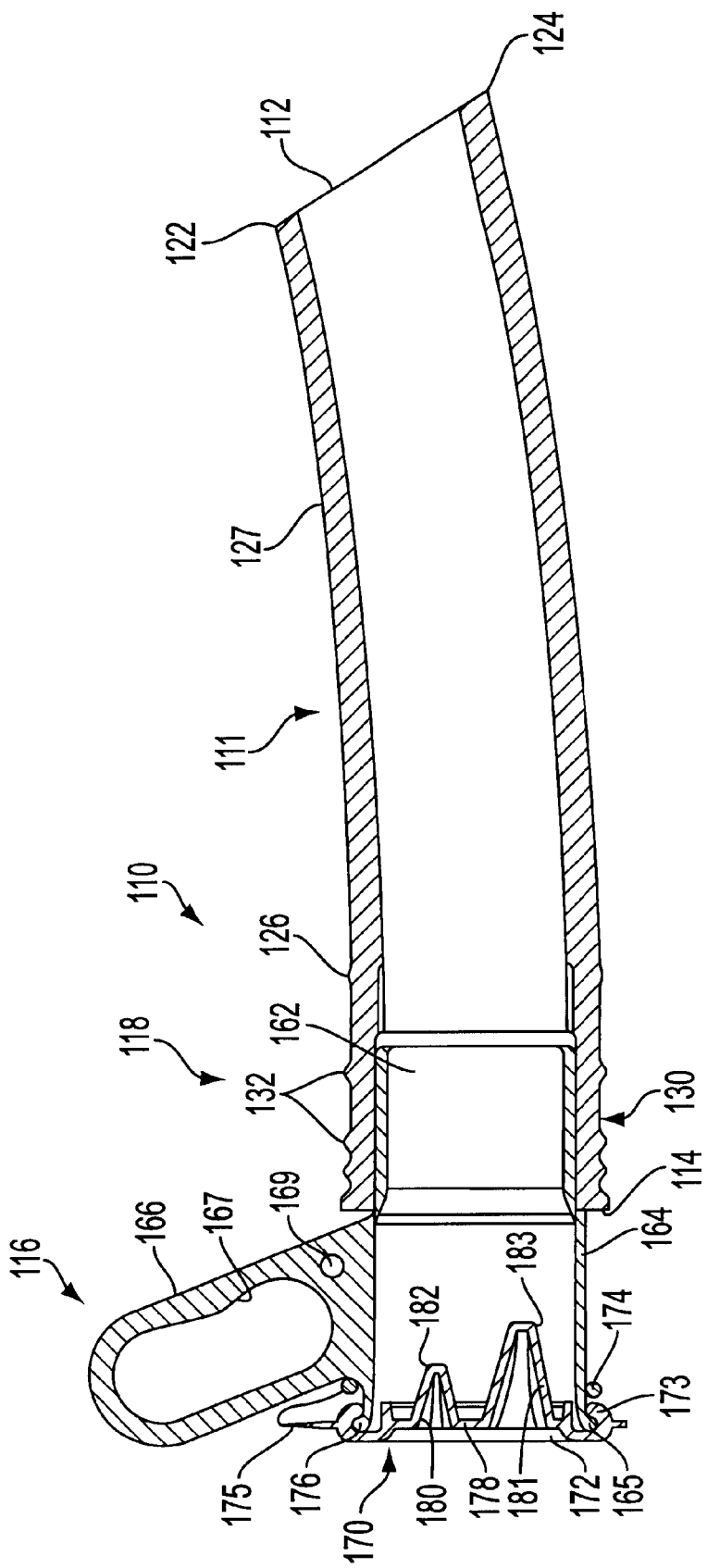
FIG. 7 is a cross-sectional view of the assembled tube of FIGS. 5 and 6.
Figure 9:
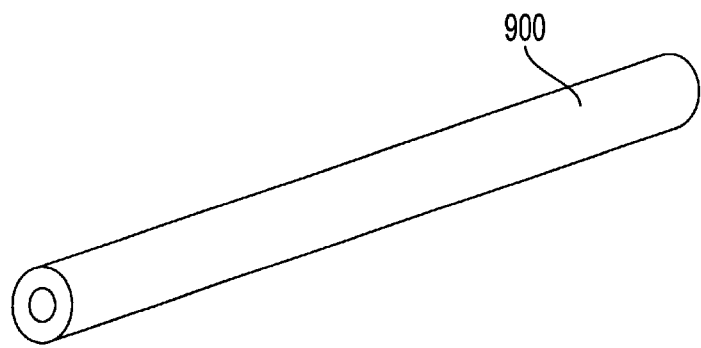
Figure 10:
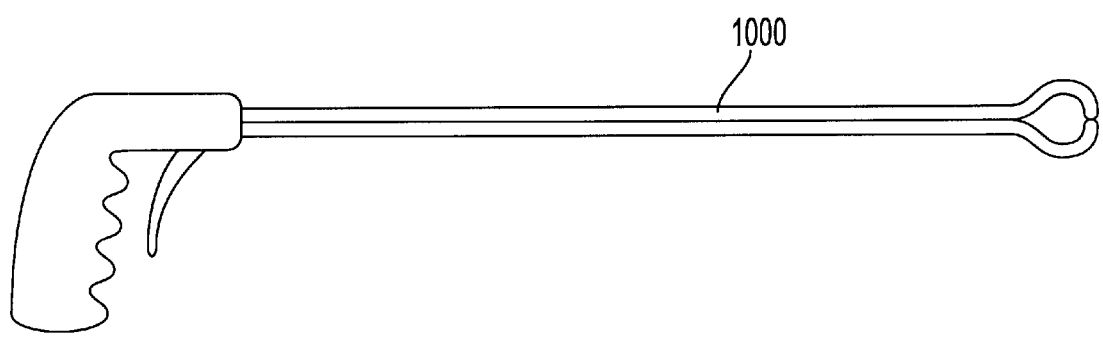

Headcap 170 has a closure disc 172 linked to a ring 174 by a thin web hinge 175: ring 174 retains the headcap on headpiece main body 164. Closure disc 172 has an annular internal channel 176 at its periphery with a rounded skirt 173 (FIG. 7). Channel 176 is sealingly engageable with a bead 165 at the open rim of headpiece main body 164. Channel 176 extends about a central web diaphragm 178 that has two, one small and one large, generally conical portal structures 180, 181. Portable structures 180, 181 can serve as valves and have respective end slits 182, 183 that are normally biased closed against fluid flow, by the resilience of the material, but may deform about and seal against an inserted surgical tool or other device. Such tools or devices include a smaller bore tube to promote washing of body fluids and tissue specimens from the interior of the tube, with or without the aid of suction, when the transvaginal tube is fitted within a subject, or an intra-uterine manipulator that is longer than the internal length of the tube and may be fixed by aids to the inside of the tube. As mentioned earlier, the distal end of this manipulator may be used to enter the cervix to allow manipulation of the cervix throughout the surgical procedure of hysterectomy or adnexal surgery.

By applying suction to the tube interior at one of portal structures 180, 181, a surgical specimen may be very effectively sucked into the tube without any need to use grasping instruments. The specimen may be, eg. the cervix and uterus, or, a deflated cyst where the cyst contents have been extracted with a needle Portal structures 180, 181, may further form a releasable sealing engagement with a fluid tight channel through which a telescope or light source may be inserted, as also referred to earlier.

Headpiece 116 and headcap 170, when assembled to tube body 111, preferably seal the end of the tube body to an extent capable of forming a fluid tight closure to approximately 5 to 30 cm water pressure, most preferably to 15 cm water pressure.

Several examples of gynaecological laparoscopic surgical procedures utilising the tube 10 or 110 will now be described.

EXAMPLE 1

A tube 10, 110 made of film or flexible smooth transparent plastic, with a valve 16, 116 mounted at one end, is sterilised in preparation for gynaecological laparoscopic surgery. When the patient is anaesthetized, positioned, cleansed and draped according to local custom, the tube is passed through the female vagina. The proximal end 12, 112 of the tube circumscribes the cervix from the vagina as depicted in FIG. 4. The tube is removed to allow the uterus and appendages to be exteriorised, following which the tube is replaced and the proximal end of the tube is intraperitoneal. The distal end 14, 114 is closed with a valve or headpiece 16, 116 and the pneumoperitoneum is maintained. No other device is needed to maintain the pneumoperitoneum but the tube is secured in place. Any fixation is acceptable but it is usually held by an assistant surgeon or one end is rested on a table. The tube is positioned according to need.

The proximal end of the tube when located intra-abdominally lies distal above the exteriorised end to allow surgical specimens to pass down the tube by gravity. The proximal end is placed close to the vaginal edges pointing slightly to the appropriate pelvic side wall during a pelvic lymphadenectomy but is placed further through the vagina for specimen removal, eg. ovarian cysts, lymph nodes and ectopic pregnancies. The surgical specimen is mobilised and placed in the mouth of the tube. It is exteriorised as it slides down the tube. In this respect tissue may be encouraged to pass down the tube by washing it with irrigation fluid.

Blood and irrigation fluid that has collected in the cul de sac may also be exteriorised through the tube. The distal end valves 180, 181 can be used to aspirate blood or body fluids from the tube or the cul-de-sac of the pelvis with an aspirating cannula. At the completion of the laparoscopic surgery the tube would be removed and the vagina closed.

EXAMPLE 2

The tube was sterilised with ethylene oxide gas. However, it will be appreciated that any method of sterilization may be employed to sterilise the apparatus.

The first steps of a true laparoscopic hysterectomy are to secure and divide the ovarian, uterine and cervical branch of the uterine artery and reflect the bladder. The uterus is separated from the vagina and its uterosacral ligaments using the tube. The tube diameter depends on the patient. A 5 cm diameter tube is ideal for multiparous and overweight women but a smaller 4 or 3.5 cm diameter tube is needed for postmenopausal and nulliparous women to make it fit the vagina. It is inserted through the introitus and advanced to the cervix. This elevates and defines the cervicovaginal junction and further bladder mobilisation can be performed at this stage if more vagina exposure is necessary. The tube position also facilitates identification of the uterine vessels for a safe point for electrocoagulation or suture occlusion and division of the vessels.

Once the vaginal wall is exposed the diathermy knife/scissors follows the rim of the tube circumcising the vagina and dividing the uterosacral ligaments. Holding the exposed cervix with laparoscopic grasping forceps and rotating the tube so that the longer bevelled end is beneath the knife puts the vagina under further local stretch. This reduces local blood flow and makes uni-polar electrocoagulation particularly efficient.

After the cervix has been separated from the vagina it is held with laparoscopic grasping forceps and fed in the open end of the vaginal tube. When the tube is slowly removed vaginally the cervix follows. The gas is then temporarily released from the peritoneal cavity to prevent any explosive spray of body fluids from the introitus as the tube and specimen are removed. If the uterus is too large to be totally inserted into the tube, just the cervix is inserted and the specimen is steered to the introitus where it can be grasped by a vulsellum and removed.

Another advantage of the tube is that the vault can be sutured laparoscopically without resorting to intracorporial knots. Replacing the tube in the vagina supports and exposes the vaginal edges. The edges can be sutured by placing a needle, preferably taper-cut with a monofilament absorbable suture, in the tube so the trailing end remains intravaginal. The needle is recovered from the tube and the first stitch passes through the inside of the vagina to the peritoneal surface. The vault is closed with a purse string or a linear closure from one end to the other and back again. When the suturing is complete the needle is returned to the transvaginal tube so that both ends of the suture are in the vagina. The tube is withdrawn leaving the needle and trailing end of the suture at the introitus so the operator can lean over and tie the ends intravaginally. Other intracorporeal or extracorporeal techniques of knot tying may be employed.

Results

The tube was used to separate the vagina from the cervix in forty cases by five different surgeons, thirty-four of these were simple laparoscopic hysterectomies for benign diseases in women with limited vaginal access, three were hysterectomies plus pelvic lymphadenectomy for endometrial cancer and three were modified radial hysterectomies for early cervical cancer. In twenty cases the vault was closed laparoscopically. There were no intraoperative complications attributable to the tube.

EXAMPLE 3

Use of the Transvaginal Tube as an Aid to Bladder Neck Surgery

At either open or laparoscopic surgery, designed to elevate the bladder neck for treatment of stress incontinence of urine in the female, by either the Birch, Cato-Murray or similar procedure, the transvaginal tube previously described can also be used without the valve at the distal end to enhance bladder neck surgery. The tube may be any length from 5 cms to 35 cm in length, made of the same clear, rigid or semi-rigid plastic as previously described.

At the time in the procedure when the para-vesical area is being prepared to expose the lateral vaginal fornices, the tube is inserted with a telescope, either a direct (0 degrees) or a forward oblique type for example, with a 30 degree angle.

This tube acts to expand the vaginal walls, particularly the vaginal fornices so that they are made more prominent and fixed so that definite identification from either the open procedure or the retro-peritoneal laparoscopic or trans-peritoneal laparoscopic approach, is enhanced. The view of the vaginal fornix on the left and right is further enhanced by trans-illumination from the vaginal aspect by the telescope light. This enables improved exposure and ability to see and reflect the bladder wall from the vaginal fornices from above because of the trans-illumination effect. It also allows enhanced identification of the para vaginal venous plexus so that the large veins can be more easily avoided by the needle and suture placed from above into the vaginal wall. Placing of the Birch or Cato-Murray type suture through the sub-mucosal layers of the vagina is made easier as the large veins of the para-vaginal wall are made more identifiable by trans-illumination. With the vaginal telescope within the tube, connected to a camera and a screen, the appropriate site selected for insertion of the suture can be seen through the wall of the tube merely by compressing the wall with the outer part of the needle before insertion of the suture. The tube allows a broader and more secure bite of the wall to be taken and puncture of the mucosal or epidermal layer by the needle can be immediately recognised on the vaginal telescope screen. The supersedes the current practice of an assistant placing a thimble covered finger in the right and left vaginal fornices while the operator places the suture in the area of the vagina over the assistant's finger. With the vaginal fornices secured, tension can then be placed on the securing sutures and an appreciation of symmetrical bladder neck elevation can be made on the screen. At present, other than by the assistant's palpation as an assessment of the elevating effect, the surgeon has no idea of the degree of elevation or the right or left symmetry that is being obtained by the procedure.

In that case, full thickness penetration by the non-absorbable suture can only be discerned by the operator or the assistant feeling contact with the metal needle with the metal thimble or noting bleeding on the assistant's glove which would indicate full thickness puncture. In that case, the needle has to be withdrawn and re-inserted into the sub-mucosal dermis of the vagina.

It should be appreciated that the scope of the present invention need not be limited to the particular scope of the embodiment described above.

EXAMPLE 4

Results

In a comparative study of Laparoscopic Versus Open Surgery in the management of Endometrial cancer reported by the Western Australian Gynecologic Cancer Service at the Annual Meeting of The Australian Society of Gynecologic Oncologists in April 1999, 126 cases treated by Laparoscopic Hysterectomy using a transvaginal tube (according to an embodiment of the invention as disclosed and claimed in the parent application) were compared to 107 cases treated by the traditional "open" Laparotomy abdominal Hysterectomy procedure. The following results were reported.

|  | Laparoscopic | Open |
|---|---|---|
| Mean Weight (Kgs) | 81 | 72 |
| Operative Time (Mins) | 139 | 137 |
| Post Operative Morbidity (No. of Cases) | | |
| Urinary Tract Infection | 1 | 11 |
| Wound Infection | 0 | 4 |
| Pneumonia | 1 | 2 |
| Pulmonary Edema | 0 | 2 |
| Venous Thrombosis | 1 | 1 |
| Stroke | 0 | 1 |
| Death | 0 | 2 |
| Post Operative Days in Hospital (mean) | 3.4 | 8.5 |
| Percent cured at mean follow up of 23 and 20 months respectively | 88.9 | 88.7 |

What is claimed is:

1. A transvaginal tube, adapted for laparoscopic hysterectomy surgery or other laparoscopic surgery involving insertion of the tube into the vaginal tract of a patient, said tube having a diameter greater than 30 mm and thereby greater than the patient's cervix whereby vaginal walls of the patient envelop at least a longitudinal portion of an external cylindrical surface of the tube to substantially seal thereagainst, the tube comprising an annular edge which lies substantially in a plane non-normal to its tubular axis to define the patient's cervico-vaginal junction, and sealing means for sealing the tube during said surgery to maintain the pneumoperitoneum; and wherein said tube includes a segment in which the wall thickness is tapered longitudinally of the tube.

2. A tube according to claim 1 wherein said seal is selectively releasable.

3. A tube according to claim 1 wherein the proximal end of the tube is bevelled.

4. A tube according to claim 1 wherein the proximal end has a smooth edge.

5. A tube according to claim 1 wherein the tube is substantially transparent.

6. A tube according to claim 1 wherein the sealing means comprises a plug or cap.

7. A tube according to claim 6 wherein the plug or cap is arranged to form a seal at the distal end of the tube effective for a pressure of approximately 5 to 30 cm of water.

8. A tube according to claim 6 wherein the plug or cap is arranged to form a seal at the distal end of the tube effective for a pressure of approximately 15 cm of water.

9. A tube according to claim 1 wherein the sealing means comprises a valve means.

10. A tube according to claim 8 wherein the valve means is in releasable engagement with the distal end of the tube.

11. A tube according to claim 9 wherein the valve means is arranged to a seal at the distal end of the tube effective for a pressure of approximately 5 to 30 cm of water.

12. A tube according to claim 9 wherein the valve means is arranged to a seal at the distal end of the tube effective for a pressure of approximately 15 cm of water.

13. A tube according to claim 9 further comprising a fluid tight channel supported in concentric arrangement within the tube, said channel being sealed at its proximal end and open at its distal end and wherein the circumferential rim of the distal end of the channel is in sealing engagement with a portal formed in the distal end of the tube thus providing a means of communication between the interior of the channel and the exterior of the tube.

14. A tube according to the claim 13 wherein the sealing engagement between the channel and the tube is effective for a pressure of approximately 5 to 30 cm of water.

15. A tube according to claim 13 further comprising a second valve means releasably engaged to the longitudinal wall of the tube.

16. A tube according to claim 1 further comprising bore tube receiving means receipt of a bore tube to facilitate washing of body fluids and tissue specimens from the proximal end of the interior of the tube.

17. A tube according to claim 16 wherein the bore tube is arranged to provide suction within the tube.

18. A tube according to claim 1 further comprising intra-uterine manipulator receiving means for receipt of intra-uterine manipulator.

19. A tube according to claim 1 wherein at least most of said tube is of substantially stiff but flexible plastics material.

20. A tube according to claim 1 wherein the tube and its longitudinal axis are slightly curved between said proximal and distal ends so that the shorter longitudinal dimension defined by said non-normal plane is on the inside of the curve.

21. A tube according to claim 20 wherein said tube includes an externally roughened region for enhanced gripping of the vagina to aid presentation of the vagina for suture closure.

22. A tube according to claim 1 including means for applying suction to the tube interior for sucking surgical specimens into the tube.

23. A tube according to claim 1 wherein said sealing means comprises a cap with at least one integral portal structure adapted to engage and seal about a surgical tool or other device.

24. A tube according to claim 23 where said integral portal structure forms valve means.

25. A tube according to claim 23 wherein said cap is hingedly linked to a ring by which it is retained on the tube.

26. A tube according to claim 23, including a tube body and a headpiece engagable with the tube body, said cap being releasably sealingly engageable with the headpiece.

27. A tube according to claim 26, further including a handle integral with said headpiece for rotational alignment of the tube in situ.

28. A tube according to claim 1, including a tube body and a headpiece engagable with the tube body.

29. A tube according to claim 28, further including a handle integral with said headpiece adapted to facilitate rotational alignment of the tube in situ.

30. A transvaginal tube as claimed in claim 1 wherein the annular edge and sealing means are positioned at respective proximal and distal ends of the tube.

31. A transvaginal tube as claimed in claim 1 wherein the length of the tube is greater than approximately 25 cm.

32. A transvaginal tube as claimed in claim 1 wherein the annular edge defines the patient's cervico-vaginal junction as viewed from the patient's abdomen.

33. A transvaginal tube as claimed in claim 1 wherein the annular edge defines vaginal fornices.

34. A method of using a transvaginal surgical device for laparoscopic hysterectomy treatment or other laparoscopic treatment involving insertion of the surgical device into a vaginal tract of a patient, the device comprising a tubular portion having a diameter greater than the patient's cervix, an annular edge which lies substantially in a plane non-normal to its tubular axis to define the patient's cervico-vaginal junction, and a sealing means capable of sealing the tube during surgery to maintain the pneumoperitoneum, said method comprising:

(i) introducing said device into a patient's vagina so that the annular edge defines a cervico-vaginal junction;

(ii) separating the cervix from the vagina; and (iii) mobilising a surgical specimen and inserting it into an end of the tube which is adjacent the annular edge.

35. The method according to claim 34 wherein the cervix is separated from the vagina by:

(i) exposing and holding the cervix with laparoscopic grasping manipulators;

(ii) inserting a knife or diathermy knife to the annular edge; and (iii) rotating the surgical device so a plane non-normal to a tubular axis stretches the vagina and at the same time cutting the cervico-vaginal junction as the surgical device is rotated.

36. The method according to claim 34 wherein the cervico-vaginal junction is defined as viewed from within the abdomen.

37. The method according to claim 34 wherein the annular edge defines vaginal fornices.

38. The method according to claim 34 wherein the vaginal walls of the patient envelop at least a longitudinal portion of an external cylindrical surface of the tubular portion to substantially seal thereagainst.

39. The method according to claim 34, further comprising the step of separating the bladder from the vagina.

40. The method according to claim 34, further comprising the step of tamponading one or more blood vessels at the cervico-vaginal junction by application of pressure to said one or more blood vessels via said annular edge.

41. A transvaginal tube, adapted for laparoscopic hysterectomy surgery or other laparoscopic surgery involving insertion of the tube into the vaginal tract of a patient, said tube being relatively stiff but flexible and having a diameter greater than 30 mm and thereby greater than the patient's cervix whereby vaginal walls of the patient envelop at least a longitudinal portion of an external cylindrical surface of the tube to substantially seal thereagainst, and a length greater than approximately 25 cm, the tube comprising an annular edge which lies substantially in a plane non-normal to its tubular axis to define the patient's cervico-vaginal junction by surrounding the patient's cervix so that the cervix protrudes into the tube, and sealing means for sealing the tube during said surgery to maintain the pneumoperitoneum; and wherein said tube includes a segment in which the wall thickness is tapered longitudinally of the tube.

42. A tube according to claim 41, wherein the tube and its tubular axis are slightly curved between said proximal and distal ends so that the shorter longitudinal dimension defined by said non-normal plane is on the inside of the curve.

43. A laparoscopic surgical device adapted for insertion into the vaginal tract of a patient, comprising a tubular portion having a diameter greater than 30 mm and thereby greater than the patient's cervix whereby vaginal walls of the patient envelop at least a longitudinal portion of an external cylindrical surface of the tubular portion to substantially seal thereagainst, an annular edge portion which lies substantially in a plane non-normal to a tubular axis of said tubular portion to define the patient's cervico-vaginal junction, and sealing means for sealing the tubular portion during surgery to maintain the pneumoperitoneum; and wherein said tubular portion includes a segment in which the wall thickness is tapered longitudinally of the tube.

44. A laparoscopic surgical device according to claim 43 wherein the annular edge portion and sealing means are positioned at respective proximal and distal ends of the tubular portion.

45. A laparoscopic surgical device according to claim 44 wherein the sealing means comprises a plug or cap.

46. A laparoscopic surgical device according to claim 45 wherein the plug or cap is arranged to form a seal at the distal end of the tubular portion effective for a pressure of approximately 5 to 30 cm of water.

47. A laparoscopic surgical device according to claim 44 wherein the sealing means comprises a valve means.

48. A laparoscopic surgical device according to claim 47 wherein the valve means is arranged to form a seal at the distal end of the tubular portion effective for a pressure of approximately 5 to 30 cm of water.

49. A laparoscopic surgical device according to claim 47 further comprising further valve means releasably engaged to a longitudinal wall of the tubular portion.

50. A tube according to claim 43, wherein the tube and its tubular axis are slightly curved between said proximal and distal ends so that the shorter longitudinal dimension defined by said non-normal plane is on the inside of the curve.

51. A transvaginal tube, adapted for laparoscopic hysterectomy surgery or other laparoscopic surgery involving insertion of the tube into the vaginal tract of a patient, said tube having a diameter greater than 30 mm and thereby greater than the patient's cervix whereby vaginal walls of the patient envelop at least a longitudinal portion of an external cylindrical surface of the tube to substantially seal thereagainst, the tube comprising an annular edge which lies substantially in a plane non-normal to its tubular axis to define the patient's cervico-vaginal junction, and sealing means for sealing the tube during said surgery to maintain the pneumoperitoneum; and wherein said tube and its tubular axis are slightly curved between said proximal and distal ends so that the shorter longitudinal dimension defined by said non-normal plane is on the inside of the curve.

52. A tube according to claim 51, wherein said tube includes a segment in which the wall thickness is tapered longitudinally of the tube.

53. A transvaginal tube, adapted for laparoscopic hysterectomy surgery or other laparoscopic surgery involving insertion of the tube into the vaginal tract of the patient, said tube being relatively stiff but flexible and having a diameter greater than 30 mm and thereby greater than the patient's cervix whereby vaginal walls of the patient envelop at least a longitudinal portion of an external cylindrical surface of the tube to substantially seal thereagainst, and a length greater than approximately 25 cm, the tube comprising an annular edge which lies substantially in a plane non-normal to its tubular axis to define the patient's cervico-vaginal junction by surrounding the patient's cervix so that the cervix protrudes into the tube, and sealing means for sealing the tube during said surgery to maintain the pneumoperitoneum; and wherein said tube and its tubular axis are slightly curved between said proximal and distal ends so that a shorter longitudinal dimension defined by said non-normal plane is on the inside of the curve.

54. A tube according to claim 53, wherein said tube includes a segment in which the wall thickness is tapered longitudinally of the tube.

55. A laparoscopic surgical device adapted for insertion into the vaginal tract of a patient, comprising a tubular portion having a diameter greater than 30 mm and thereby having greater than the patient's cervix whereby vaginal walls of the patient envelop at least a longitudinal portion of an external cylindrical surface of the tubular portion to substantially seal thereagainst, an annular edge portion which lies substantially in a plane non-normal to a tubular axis of said tubular portion to define the patient's cervico-vaginal junction, and sealing means for sealing the tubular portion during surgery to maintain the pneumoperitoneum; and wherein the tubular portion and its tubular axis are slightly curved between said proximal and distal ends so that the shorter longitudinal dimension defined by said non-normal plane is on the inside of the curve.

56. A tube according to claim 55, wherein said tubular portion includes a segment in which the wall thickness is tapered longitudinally of the tube.

* * * * *